United States Patent [19]
Pendergrass et al.

[11] 4,173,131
[45] Nov. 6, 1979

[54] POROUS ELASTIC BANDAGE

[75] Inventors: John E. Pendergrass, Seneca; David T. Melton, Walhalla, both of S.C.

[73] Assignee: The Kendall Co., Walpole, Mass.

[21] Appl. No.: 960,906

[22] Filed: Nov. 15, 1978

Related U.S. Application Data

[63] Continuation-in-part of Ser. No. 917,267, Jun. 20, 1978, abandoned, which is a continuation of Ser. No. 829,130, Aug. 30, 1977, abandoned, said Ser. No. 829,130, is a continuation-in-part of Ser. No. 746,360, Dec. 1, 1976, abandoned.

[51] Int. Cl.$^2$ .................... D04B 7/12; D04B 9/12; A61L 15/00
[52] U.S. Cl. .................................. 66/192; 66/193; 128/156
[58] Field of Search ............ 66/170, 192, 193, 195; 128/156

[56] References Cited

U.S. PATENT DOCUMENTS

| 889,827 | 6/1908 | Teufel | 128/156 X |
|---|---|---|---|
| 3,040,551 | 6/1962 | Urlaib | 66/170 |
| 3,448,595 | 6/1969 | Baltzer et al. | 66/195 X |
| 3,965,703 | 6/1972 | Barnhardt | 66/193 |
| 4,000,959 | 3/1977 | Wall et al. | 66/193 |

FOREIGN PATENT DOCUMENTS

| 1282608 | 7/1972 | United Kingdom | 66/195 |
|---|---|---|---|
| 1378426 | 12/1974 | United Kingdom | 66/195 |

OTHER PUBLICATIONS

Darlington, K. D.; *Factors Affecting Elasticity of Warp Knitted Fabrics,* in Knitting Times, 40(48): pp. 39–40, Nov. 22, 1971.

*Primary Examiner*—Henry Jaudon
*Assistant Examiner*—Andrew M. Falik

[57] ABSTRACT

A lightweight, porous knitted elastic bandage is produced from a warp of false-twist synthetic yarns with a filling inlay of regular yarns. The filling yarns are arranged in varying patterns across the warp yarns so that a portion of their length lies in looped and cursive configuration upon the surface of the bandage, and the structure is so open that overlapping layers of the bandage cling to each other in substantially non-displaceable relationship.

6 Claims, 12 Drawing Figures

POROUS ELASTIC BANDAGE

This application is a continuation-in-part of our co-pending application Ser. No. 917,267, filed June 20, 1978 now abandoned, which in turn is a continuation of our application Ser. No. 829,130, filed Aug. 30, 1977, now abandoned, said Ser. No. 829,130 being in turn a continuation-in-part of our application Ser. No. 746,360, filed Dec. 1, 1976, now also abandoned.

This invention relates to a knitted elastic bandage for surgical or supportive purposes. More particularly, it relates to a knitted bandage of a lightweight open, porous nature in which overlapping layers cling to each other to form a relatively non-slipping type of support.

BACKGROUND OF THE INVENTION

Historically, elastic bandages have been made in a woven structure, using narrow or ribbon looms, wherein the retractive and supportive power has been supplied by special warp yarns. Early bandages employed overtwisted cotton warp yarns, as shown in the Teufel 1908 U.S. Pat. No. 889,827, or in the Klein 1932 U.S. Pat. No. 1,875,740.

The use of cotton warp yarns has been displaced to a considerable extent by the use of elastomeric warp yarns, initially of extruded or cut rubber, more recently of other elastomeric manmade polymers. Such elastomeric warp yarns are usually wrapped with a layer of non-elastomeric filaments.

Such bandages, although effective in use, suffer from the disadvantage of being relatively expensive. They are produced singly on a narrow loom, utilizing expensive wrapped elastomeric yarns, at comparatively slow production rates inherent in the weaving process.

In an attempt to circumvent the limitations of the weaving process, it has been proposed to produce elastic bandages in a knitted structure, as in U.S. Pat. No. 3,965,703, to Barnhardt.

The knit structures thus far, however, still employ elastomeric yarns as part of the warp structure, and customarily employ very heavy filling yarns to prevent necking-in of the bandage when stretched. They are relatively heavy in weight, averaging 6 to 12 oz. per square yard (204 to 408 grams per square meter), and due to their compact structure they become hot and uncomfortable to wear. Also, when applied to a limb or other body member they must be secured in place in the outer wrap by means of some sort of fastening, such as toothed metal clips. As the bandage is worn, the layers of the bandage tend to slip and slide past each other, leading to the undesirable alternatives of frequent removal and rewinding or else winding the bandage with an uncomfortable degree of tension.

It is with improvements in the production of bandages of this type that the present invention is concerned.

SUMMARY OF THE INVENTION

It has been found that by the utilization of so-called false twisted filament yarns in the warp of long direction, with a staggered inlay of regular yarns in the cross direction, a new type of elastic bandage can be produced which has stretch and power characteristics comparable with the characteristics of conventional elastic bandages of woven structure.

By false-twist yarns is meant a type of texturized continuous filament yarn which has been given increased bulk and loft, together with stretch, by the introduction into the yarn of crimps, loops, coils, and crinkles by false-twisting. Such yarns are commercially produced by well-known processes, and when the filamentary material is thermoplastic, as is the case with nylon, a heat-setting stage in the false-twist process renders the stretch and the crimped configuration of the yarn relatively permanent.

Depending on the direction of rotation of the spindle, the yarn may be twisted clockwise or counterclockwise, giving rise to S-twist or Z-twist in the yarn. It is customary to employ yarns of both types of twist where it is desired to minimize torque and twist in a fabric, either as alternate warp yarns or as a yarn of one twist plied with a yarn of opposite twist.

The warp yarns in the preferred bandage of this invention consist of false-twist S or Z yarns, knitted in a chain stitch with a false-twist Z or S yarn inlay. In order to minimize the tendency of knitted fabrics to narrow in when stretched, the chain-stitched warps are held in position by a series of interlocking filling yarns of conventional non-elastic type, preferably spun yarns, inlaid in a particular set of varying patterns which will be described more fully herein below.

DESCRIPTION OF THE INVENTION

The invention will be understood more fully with reference to the following description and drawings, in which.

Figure 3:
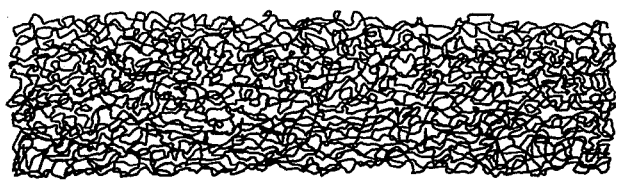
FIG. 3 is a highly magnified view of a false-twist yarn used in the process of this invention.

For the sake of clarity, the involved nature of the false-twist warp yarns is shown only in FIG. 3. Referring now to FIG. I, a preferred bandage of this invention comprises a set of warp yarns 10, interconnected by filling yarns 12 which are interlocked with at least a majority of the chain loops of the warp yarns. The bandage is of an open, porous construction, having an air porosity usually in excess of 500 cubic feet of air per square foot per minute at 0.5 inches of air pressure, as tested on the Frazier air permeability device (18 cubic centimeters per square centimeter at 5 centimeters). This porosity is in part due to the lightweight of the bandages of this invention, which customarily lies in the range of 2 to 3 oz. per square yard (68 to 102 grams per square meter), compared with conventional elastic bandage which weigh 6 to 12 oz. per square yard (204 to 408 grams per square meter).

The lightweight and open weave nature of the preferred bandages of this invention have been found to minimize the tendency of the false-twist inlay yarns of a given type of twist, S or Z, to impart curl to a bandage, provided that the inlay yarns are combined with a chain stitch yarn of opposite twist. For simplicity in manufacture, therefore, it is desirable to utilize warp yarns of a composite nature, wherein each composite yarn consists either of a chain stitch S yarn with a Z twist inlay, or a Z twist yarn with an S twist inlay.

Figure 1:
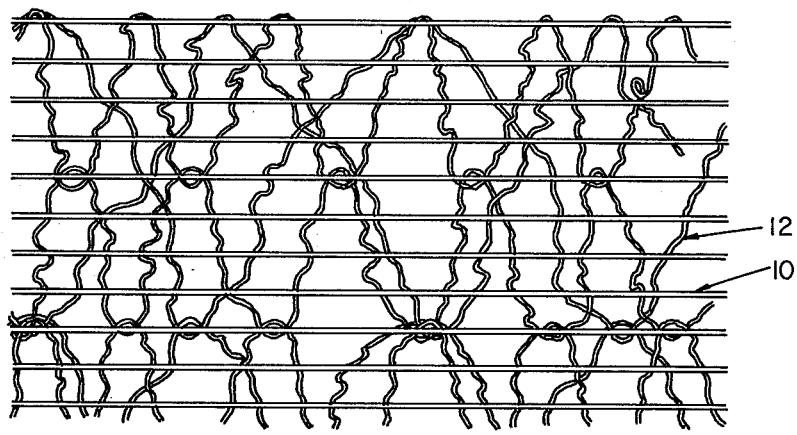
FIG. 1 is a magnified isometric view of a segment of a preferred bandage of this invention in relaxed state.
Figure 2:
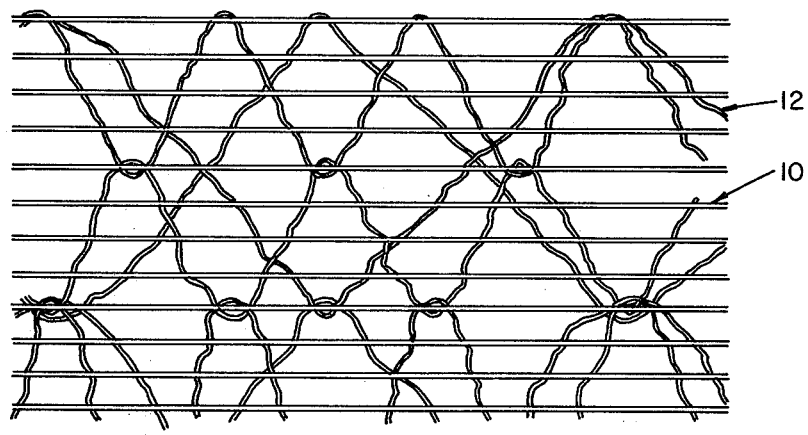
FIG. 2 is a magnified view of a portion of such a bandage under 50% extension.
Figure 5:
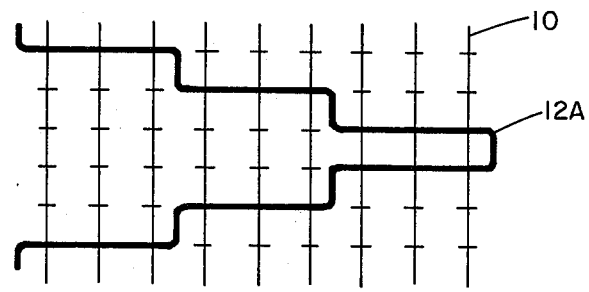
FIGS. 5, 6, 7 and 8 represent the paths of the individual filling yarns in one repeat of a preferred embodiment of this invention.
Figure 6:
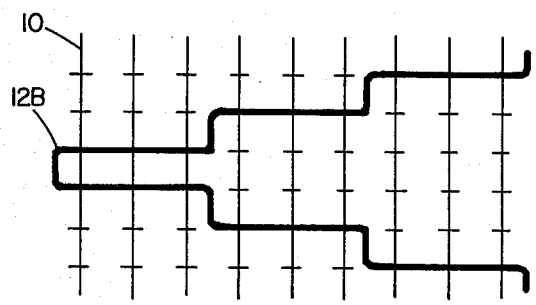
Figure 7:
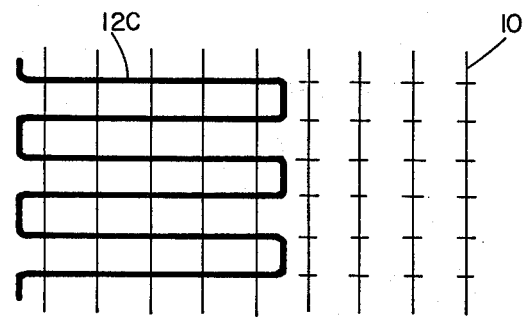
Figure 8:
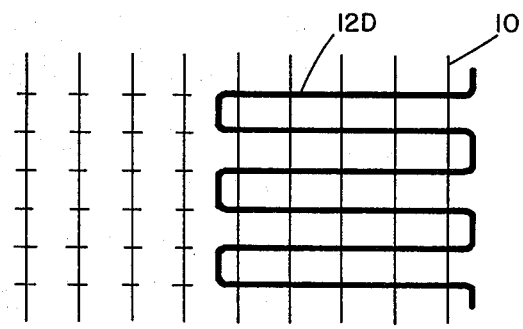
Figure 10:
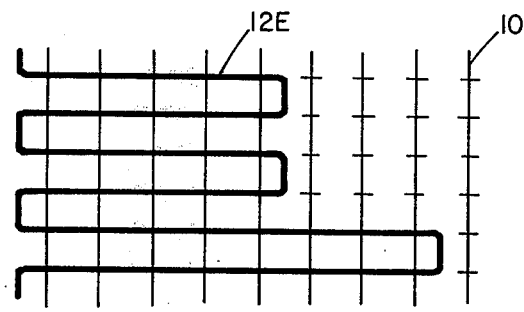
FIGS. 10 and 11 represent the paths of the individual filling yarns in one repeat of a second embodiment of the invention.
Figure 11:
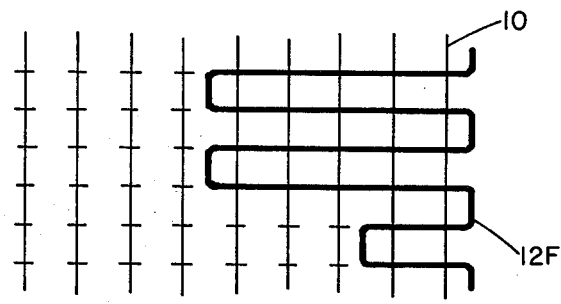

The filling yarns 12 in FIG. 1 are shown as lying slack, in cursive or looped configuration on the surface of the bandage. This relaxed condition of the filling yarns is important in that it allows the elasticity of the false-twist yarns 10 to be utilized without any substantial necking-in or widthwise contraction when the bandage is stretched. It is due in part to a heat-shrinkage process to which the bandage is subjected after it comes from the warp-knitter or crochet machine. Probably in greater part, however, the relaxed condition of the filling yarns is due to the unusual manner in which the lightweight filling yarns are deployed through the warp yarns, as shown schematically in FIGS. 5, 6, 7, and 8 the arrangement of the individual filling yarns in a preferred embodiment of the invention, and in FIG. 9 a composite of all four filling yarns, each governed by an individual guide bar. In the bandages of this invention the filling yarns do not progress in uniform fashion across the warp yarns, as in prior art elastic bandages, but are arranged in offsetting pairs across the bandage. The pairs may be arranged in diagonal fashion, as in FIGS. 5 and 6; in reciprocating fashion, as in FIGS. 7 and 8; in staggered fashion, as in FIGS. 10 and 11; or in various combinations of these. Each individual filling yarn extends over only a portion of the warp yarns: as illustrated in FIGS. 5 and 6, the filling yarns 12A and 12B are inlaid in 9 warp yarns, in a preferred embodiment of the invention, while the filling yarns 12C and 12D of FIGS. 7 and 8 are inlaid in 5 warp yarns. Since there are 14 yarns per inch in this bandage, a bandage four inches wide will contain 7 pairs of filling yarns 12A and 12B and 11 pairs of yarns 12C and 12D.

Figure 9:
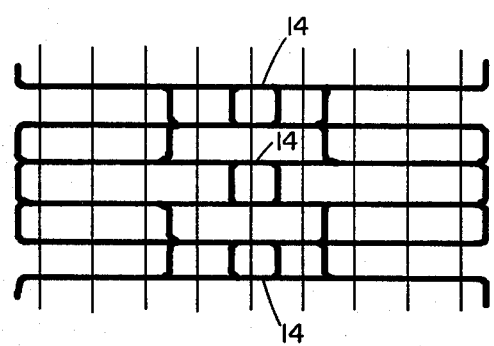
FIG. 9 is a composite of FIGS. 5, 6, 7 and 8.

Yarns 12C and 12D both terminated their lateral path on a common yarn: as shown in FIG. 9, at 14, this is the fifth warp yarn in a nine-yarn repeat.

PREFERRED EMBODIMENT OF THE INVENTION

Using a crocheting machine, a bandage was constructed utilizing five yarn guide bars per repeat operating in a vertical plane perpendicular to the horizontal needles, four of the bars moving across the width of the fabric to insert the filling yarns of 30/1 cotton and the fifth bar being utilized to insert the inlaid false-twist yarn 10A or 10B. The filling yarn pattern was that shown in FIGS. 5, 6, 7 and 8, each of the guide bars operating independently. The composite false-twist yarns 10 were 70/1/17 Z twist inlay and 70/1/17 S twist chain stitch Superloft nylon, a trade name for false-twist yarns made on a Leesona false-twist apparatus. There were nine warp yarns in each repeat, a total of 57 needles being used in the production of a four-inch (10 centimeter) bandage with 14 composite warp yarns per inch (5.5 yarns per centimeter). The filling yarn of 30/1 cotton was inserted at the rate of 17 picks per inch (6.7 yarns per centimeter).

Figure 4:
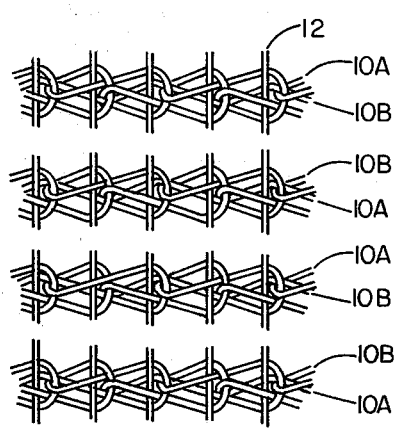
FIG. 4 is a formalized representation of the interrelationship of the warp and filling yarns in the bandages of this invention.

As seen in FIG. 4, the cotton filling yarn is inlaid into each of the loop-forming S yarns in the composite warp yarns. FIGS. 5, 6, 7, and 8 illustrate the particular patterns with which each of the four filling yarns is deployed, to form the composite filling yarn structure shown in FIG. 9.

The bandage as formed on the machine has a weight of about 60 grams per square yard or 72 grams per square meter. It is then conditioned by exposing it, untensioned, to moist steam at about 140° F. (60° C.) for one to two hours, after which it is dried. During this steaming process the bandage undergoes shrinkage, increasing in weight to about 70 grams per square yard or 84 grams per square meter. In addition, the filling yarns are relaxed from their off-machine regular configuration to the cursive configuration shown in FIG. 1. This relaxation builds slack into the filling yarns, and in part accounts for the ability of the bandage to be stretched without an accompanying decrease in width.

The finished bandage had an air porosity of over 900 cubic feet of air per square foot per minute at 0.5 inches pressure, as tested on the Frazier air permeability apparatus (32 cubic centimeters per square centimeter per minute at 5 centimeters pressure).

At 100% elongation the bandage had 9 picks or filling yarns per inch (3.5 per centimeter) with 14 composite warp yarns per inch. Since the filling yarns were 30/1, the filling cover factor was about 2, an extremely low factor characteristic of open-mesh netting. Cover factor is a measure of the degree of openness of a fabric, and is calculated as the number of yarns per inch divided by the square root of the yarn count in the cotton system. In the bandages of this invention, the number of filling yarns per inch of bandage under 100% extension preferably lies within the range of 8 to 20 (3 to 7.5 per centimeter) with the filling yarns ranging from 20's to 60's in count, so that the cover factor is less than 5.

This low cover factor in the filling brings the crimped, curled and looped nature of the warp yarns into prominence as a dominant surface characteristic of the bandages of this invention. When the bandage is applied to a body member in the customary overlapping layer procedure, each layer of the bandage clings firmly to each adjacent layer with which it is in contact, due to the interlocking of the crimps and curls of the warp yarns in one layer with the warps in adjacent layers and with the open, widely-spaced filling yarn structure. Thus the bandage resists slipping and displacement as the body member is flexed during movement, an advantage not present in conventional elastic bandages.

OTHER EMBODIMENT OF THE INVENTION

Figure 12:
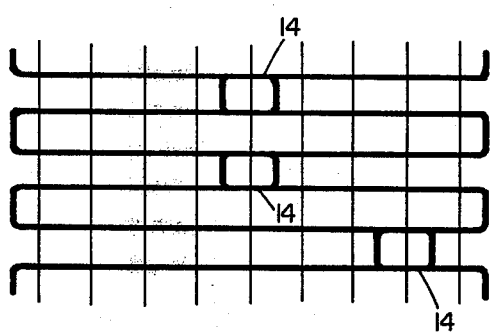
FIG. 12 is a composite of FIGS. 10 and 11.

Using warp yarns of 70 denier 23 filament false-twist nylon, arranged in the same S and Z twist patterns as in the preferred example above, a bandage was constructed utilizing three guide bars. Two bars inserted the 30/1 cotton filling yarns in the patterns shown at 12E and 12F in FIGS. 10 and 11. The overlap of these yarns is shown at 14 in FIG. 12, a composite of FIGS. 10 and 11. Again there were nine warp yarns per repeat. Since only two filling yarns were employed, the third guide bar was changed from throwing one needle per link to two needles per link, so that adjacent warp yarns were held together not only by the filling yarns but by the inlay false-twist yarn 10A or 10B of FIG. 4.

After relaxation by steaming, the bandage weighed 63 grams per square yard (76 grams per square meter), with 16 warp yarns and 21 filling yarns per inch (6 warp yarns and 8 filling yarns per centimeter). The porosity was in excess of 500 cubic feet of air per square foot per minute at 0.5 inches pressure (18 cubic centimeters per square centimeter at 5 centimeters pressure).

Typical bandages of this invention are characterized by an ability to be stretched in substantially the same range as conventional elastic bandages, a representative range being 60% stretch under a force of 10 pounds (4.5 kg.) up to 170% stretch under a force of 50 pounds (22.5 kg.). In addition to being lightweight and comfortable to wear, due to their porosity, they are absorbent, and are easy to wash and sterilize. Since they contain no rubber or synthetic elastomeric material, they may be used in cases where elastomer yarns in contact with the skin give rise to an allergenic reaction.

It will be appreciated by those skilled in the art that, unlike the production of woven bandages on a narrow loom, the knitted bandages of this invention may be produced on a wide flat-bed machine, and that a plurality of bandages, of varying widths if desired, may be produced in a single machine operation using a tie-in yarn between individual bandages if necessary, said yarn being readily removed subsequently by an unraveling operation.

The above description of the bandage is to be regarded as exemplary only, and other sizes of yarn and knitting patterns may be utilized without departing from the spirit of the invention.

What is claimed is:

1. A self-supporting, open mesh knitted elastic bandage characterized by the tendency of overlapping layers of the bandage to cling to each other in relatively non-displaceable relationship, which comprises a set of composite parallel warp yarns comprising a first false-twist yarn formed into stitch loop chains with a second false-twist yarn inlaid into the loops of said first false-twist yarn, said second false-twist yarn being of opposite twist from the twist of said first false-twist yarn, and a plurality of individual filling yarns describing varied and cursive patterns across said set of composite warp yarns and being inlaid therewith, said varied and cursive patterns of filling yarns overlapping one with another across a substantial portion of the width of said bandage, no individual filling yarn pattern extending across more than a minor portion of the width of said bandage, and a portion at least of the length of said filling yarns lying in slack looped configuration on the surface of said bandage.

2. The bandage according to claim 1 in which the filling yarn cover factor is less than 5 when the bandage is under 100% extension.

3. A bandage according to claim 1 in which the warp yarns are of heat-set thermoplastic material.

4. A bandage according to claim 1 in which the warp yarns consist alternately of chain-stitch false-twist S yarns with a false-twist Z yarn inlay and chain-stitch false-twist Z yarns with a false-twist S yarn inlay.

5. The bandage according to claim 1 in which pairs of filling yarns are arranged in reciprocating diagonal fashion across a plurality of said warp yarns, and other pairs of filling yarns are arranged in alternating mirror-image fashion across a plurality of said warp yarns, said filling yarns overlapping with each other across a substantial portion of said warp yarns.

6. The bandage according to claim 1 in which a multiplicity of pairs of filling yarns are arranged in reciprocating staggered and overlapping fashion across a plurality of said warp yarns.

* * * * *